US006939558B2

(12) United States Patent
Massara et al.

(10) Patent No.: US 6,939,558 B2
(45) Date of Patent: Sep. 6, 2005

(54) INTRAVAGINAL DEVICES CONTAINING PROGESTERONE FOR ESTRUS SYNCHRONIZATION AND RELATED PROCESES

(75) Inventors: Julio Eduardo Massara, PCIA. De Buenos Aires (AR); Nestor Gerardo Massara, PCIA. De San Luis (AR); Victor Oscar Dvoskin, PCIA. De Buenos Aires (AR)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/922,493

(22) Filed: Aug. 19, 2004

(65) Prior Publication Data

US 2005/0021009 A1 Jan. 27, 2005

Related U.S. Application Data

(63) Continuation of application No. 10/176,801, filed on Jun. 21, 2002, now Pat. No. 6,805,877.

(30) Foreign Application Priority Data

Oct. 24, 2001 (AR) ........................................ P010104978

(51) Int. Cl.[7] ........................................ A61F 6/06
(52) U.S. Cl. ........................................ 424/430; 128/833
(58) Field of Search ........................................ 424/422, 430, 424/432, 433, 438; 128/833, 839; 604/890.1, 891.1, 892.1

(56) References Cited

U.S. PATENT DOCUMENTS

| | | | |
|---|---|---|---|
| 3,710,795 | A | 1/1973 | Higuchi et al. |
| 3,938,515 | A | 2/1976 | Leeper et al. |
| D241,078 | S | 8/1976 | Okamoto et al. |
| 3,995,631 | A | 12/1976 | Higuchi et al. |
| 4,012,496 | A | 3/1977 | Schopfin et al. |
| 4,144,317 | A | 3/1979 | Higuchi et al. |
| 4,188,951 | A | 2/1980 | Higuchi et al. |
| 4,249,531 | A | 2/1981 | Heller et al. |
| 4,292,965 | A | 10/1981 | Nash et al. |
| 4,326,511 | A | 4/1982 | Zimerman |
| 4,449,980 | A | 5/1984 | Millar et al. |
| 4,629,449 | A | 12/1986 | Wong |
| 4,649,042 | A | 3/1987 | Davis et al. |
| 4,888,074 | A | 12/1989 | Pocknell |
| 4,961,931 | A | 10/1990 | Wong |
| 6,423,039 | B1 | 7/2002 | Rathbone et al. |
| 6,444,224 | B1 | 9/2002 | Rathbone et al. |
| 6,663,608 | B2 | 12/2003 | Rathbone et al. |

*Primary Examiner*—Sharon Kennedy
(74) *Attorney, Agent, or Firm*—William P. Ramey, III

(57) ABSTRACT

Embodiments of the present invention generally relate to devices and processes related to estrus synchronization. Particular embodiments of devices and processes of the present invention slowly release progesterone over a period of time for estrus synchronization.

22 Claims, 2 Drawing Sheets

INTRAVAGINAL DEVICES CONTAINING PROGESTERONE FOR ESTRUS SYNCHRONIZATION AND RELATED PROCESES

RELATED APPLICATION

The present application is a divisional of U.S. Ser. No. 10/176,801, filed on Jun. 21, 2002, now U.S. Pat. No. 6,805,877, which claims priority from an application filed in Argentina on Oct. 24, 2001, under application number P 01 01 04978.

FIELD OF THE INVENTION

The present invention generally relates to devices and processes for estrus synchronization in an organism.

BACKGROUND OF THE INVENTION

Beef Cattle

The productive cycle of a breeding cow can be divided in three periods:

a) Period of dry cow b) Calving preparatory period c) Calving and lactation

Every period has specific nutritional requirements and hormonal characteristics. The pregnancy of the animals involves a substantial cost since the requirements of the last month of gestation are higher than those applicable to a non-pregnant animal.

Besides, if calving is taken as Day 0 of the calendar year, the more synchronic the 0 Days of a herd, the better will the fodder supply adjust to the nutritional needs of the herd, thus improving the physiological needs of the cattle and at the same time addressing an economic issue.

Likewise, the post-calving anestrus period can be shortened allowing for the estrus to occur at the end of the puerperium period. In this way, animals can be served and fertilized quicker, improving not only the corporal condition of the herd and the pregnancy but also the health and welfare of calves because of a reduction of the mother's stress factors.

The advantages and benefits of a planned reproductive management program are known and can be generally stated as, which may or may not be effected in every planned reproductive management program:

1. Allows for planning of calving dates.
2. Improves the rotational grazing and ensures an efficient distribution of fodder to meet the physiological feeding needs of the cattle.
3. Facilitates the design of calving and service plots and optimizes the work of the personnel.
4. Decreases the number of bulls per herd, allowing for the investment in bulls with superior genetics and quality.
5. Improves the work with the calves, allowing for their distribution in homogenous groups.
6. Enhances the sustainability of the estrus system, thus avoiding dependence on natural periods.
7. Allows for a strategic supplementation management of the herd and optimizes supplemental doses.
8. Facilitates compliance with the vaccination program and improves its efficiency.
9. Shortens the service season and allows to produce one calf per cow served per year.

10. Facilitates the use of artificial insemination at a large scale, the application of an improved genetics and the practice of industrial cross-breeding.
11. Allows for a fixed-time artificial insemination process, without estrus detection.
12. Facilitates the control of returns to service.
13. Increases the fertility rate in heifers and allows for the insemination of a high number of animals per day.
14. Facilitates the insemination of animals with deficient estrus onset.
15. Facilitates the insemination of 15-month animals even when their luteus phases are not mature yet.
16. Facilitates the synchronization of receptors for embryo transfer.
17. Gives economic benefits.

REPRODUCTIVE EFFICIENCY OF THE BREEDING CATTLE

The productivity of the breeding cattle depends largely on its reproductive efficiency. The former is measured in terms of kilogram of calf per served cow while the latter is measured in terms of pregnancy rate or percentage. However, the most important parameter to individually evaluate the reproductive efficiency is the interval between calvings that, in economic terms, should not exceed the optimum period of 365 days, that is to say, a calf per cow per year. The main determining factor of the calving interval is the calving-conception interval that, considering a constant pregnancy period of 280 days, should not exceed 80–85 days, in most breeding facilities and most climates.

Some quantitative ratios between these parameters have been already established and the observations show that the pregnancy percentage falls linearly when the calving-estrus interval increases from 60 to 120 days. This calving-first estrus relationship shows that calf kilograms decrease considerably when such interval is extended and the loss amounts to 833 g per day.

Naturally, management decisions and procedures have some influence on the calving-conception interval but the latter is mainly determined by the following three factors:

1. The reestablishment of ovarian cycles after calving.
2. The occurrence of the estrus at the proper time of the cycle
3. The pregnancy rate after the service.

In this ratio, the pregnancy rate increases almost linearly when the estrus fertility increases. The slope depends on the calving-estrus interval, and it increases when this interval shortens.

When the calving-estrus interval is 60 days, a fertility increase, for example by reducing the services from three to two per served cow, results in a 16% increase in pregnancy percentages. The analysis of these quantitative ratios illustrates the impact of these parameters on the productivity of a breeding herd. Therefore, it is worth analyzing the way in which environmental factors influence the calving-conception interval.

DAIRY CATTLE

The benefits of a planned reproductive management in dairy cattle include the predetermination of the calving date and, therefore, of production; the possibility of facilitating the implementation of artificial insemination by reducing the estrus detection tasks and increasing the overall reproductive efficiency of the breeding operations.

The adoption of estrus cycle handling systems in dairy cows is increasingly important nowadays if we consider the need of streamlining the productive systems by improving production during the life of the animal and reducing the calving-conception intervals since this process results in an increase in the number of productive days of the animals. Given the fact that the grazing production systems of our country have a natural seasonality, cows must be fertilized at predetermined dates.

It has been said that the adoption of a scheduled reproductive management system improves the reproductive efficiency of the herds. Therefore, in various operations suitable parameters may include:

| Parameters | Objectives |
|---|---|
| Calving interval | 12.4–12.7 months < 13 |
| Days of open cows | 95–105 days |
| Lactation days (per herd) | 155–165 days |
| % cows with over 150 days empty | <8% |
| Annual % of cows discarded due to infertility | <5% |
| Lactation days up to 1st service | 60–65 days |
| % Estrus detected after 24 days | 80–85% |
| % Empty at pregnancy test | <10% |
| % Conception after 1st service | >50% |
| Services per conception | <2.2 |
| % Pregnant cows with 3 services or less | 85–88% |
| % Cows returning after 4th service or more | <15% |
| Minimum calving-conception interval in the future | <100 |

Out of all the abovementioned, the most frequently used parameters to evaluate the reproductive management programs are the days of open cows and the calving-conception interval. The former implies loss of income due to the fact that there are less lactation days and less calves per year. In normal cows, an open cow day consists of the physiological puerperium, that is to say the amount of days required for the first estrus to appear after calving, normally 10 days at least. This period, also called Voluntary Wait Period, cannot be substantially modified because it depends on physiological variables. The other components of these open cow days originate in estrus detection failures and conception failures and, in both cases, involve the addition of 21 days or more of the new estrus cycle to open cow days.

Therefore, a main reason to adopt a reproductive management program for dairy herds is the optimization of estrus detection and the improvement of conception rates.

POST-CALVING REPRODUCTIVE MANAGEMENT IN DAIRY COWS

During the post-calving period, dairy cows suffer an important change in their energy balance prior to the onset of the normal ovarian cycles. This negative energy balance is largely caused by the loss of energy resulting from lactation, larger than the energy that can be regained with food. This negative balance is associated to the hormonal plasma profiles determining a lower activity in the follicular dynamics and resulting in lack of estrus and ovulation. The reestablishment of LH pulsatile secretion after calving produces the restart of the normal follicular dynamics. The early beginning of the estrus cycles becomes a determining factor of an early conception. The moment of the first ovulation determines and limits the number of estrus cycles that are likely to occur before the first insemination, and the higher the number of estrus before the 60-day post-calving period, the higher the chance of conception at the first service (2.60 and 1.75 services per conception for cows of 0 and 4 estrus respectively before the 60-day post-calving period). The objective of the producers should be to fertilize the cow in the first or second insemination; otherwise, the number of open cow days would increase and the calving-conception period would be longer with the resulting production losses. An early presence of plasma progesterone prepares the uterus and the follicles for the cycles after the first ovulation to be complete and normal, therefore facilitating an early conception. It has been illustrated that low concentrations of progesterone (early post-calving) are associated to short anovulation cycles. Instead, high concentrations of progesterone are associated to normal and long cycles and normal ovulations. High progesterone concentrations (1 ng/ml) obtained through the application of intravaginal devices impregnated with progesterone result in this follicular replacement, inducing a normal differentiation at the level of the granulosa cells, determining the onset of the cycle and the development of a corpus luteus with normal luteal phases. The mechanism involves the increase in the frequency of LH pulses and of its action on the production of follicular estrogens, the development of LH receptors and the luteinization. In short, the beneficial effects of the treatments based on intravaginal devices after calving result in an anticipation of the normal cycles, therefore reducing the amount of open cow days and the calving-conception interval.

NEUROENDOCRINE CONTROL OF THE ESTRUS CYCLE

The estrus cycle is regulated by a hormonal interaction ruled by the hypothalamus-hypophysis-ovary-uterus axis.

Hypothalamus

The hypothalamus forms the basis of the brain and its neurons produce the gonadotropin-releasing hormone or GnRH. This hormone spreads to the capillaries of the hypophysial portal system and from there to the cells of the adenohypophysis where it stimulates the synthesis and secretion of the hypophysial hormones, FSH and LH.

Hypophysis

It is formed by a frontal portion or adenohypophysis and a rear portion or neurohypophysis. The former produces several types of hormones, out of which FSH and LH play an essential role in the neuroendocrine control of the estrus cycle. The FSH hormone is responsible for the ovarian steroid genesis and the growth and maturation of the follicles, while the LH takes part in the ovarian steroid genesis process, the ovulation and the formation and maintenance of the corpus luteus. These hormones are secreted to the blood stream by means of pulses and are regulated by two systems: the tonic system and the cyclic system. The former produces the circulating basal level of hypophysial hormones which promote the development of the germinal and endocrine elements of the gonads. The cyclic system operates more sharply and becomes evident only during 12 to 24 hours in each of the reproductive cycles of the cow. The essential function of the cyclic mode is to cause the ovulation.

The neurohypophysis stores the oxytocin produced by the hypothalamus. This hormone takes part in several functions such the calving mechanism, the initiation of milk production and the transportation of the sperm. It is also presumably involved in the luteolysis.

Ovaries

The ovaries are exocrine glands (they release the ova) as well as endocrine glands (they secrete hormones). Among the hormones produced by the ovaries we can mention the estrogens, the progesterone and the inhibin. The estrogens—steroid hormones—are produced by the ovarian follicle and act on different target organs such as the Fallopian Tubes, the uterus, the vagina, the vulva and the central nervous system, where they stimulate the estrus behavior, and the hypothalamus, where they produce a negative feedback on the tonic center and a positive feedback on the cyclic center.

The progesterone—steroid hormone—is produced by the corpus luteus because of the action of the LH. The effects of the progesterone are observed once the white tissue has been exposed for some time to estrogen stimulation. This preparation by the estrogens leads to a synergic effect.

This hormone prepares the uterus for the embryo implant and the gestation. At the hypothalamus level, it produces a negative feedback on the tonic center.

The inhibin—a protein hormone—is produced by the ovarian follicle (granulosa cells) and takes part in the FSH secretion regulation mechanism. It generates a negative feedback at the hypophysis level, resulting in a reduced FSH secretion.

Uterus

The uterus produces the prostaglandin F2α (PGF2α) that takes part in the neuroendocrine regulation of the estrus cycle because of its luteolytic effect. It also takes part in the ovulation and calving mechanisms.

PHASES OF THE ESTRUS CYCLE

A description of the main events in the estrus cycle is included as follows.

The estrus cycle can be divided in three phases: 1) Follicular or luteal regression phase (proestrus), 2) periovulatory phase (estrus and metaestrus) and 3) luteal phase (diestrus).

Day 0 of the estrus cycle is the estrus day, that is to say the day on which the estrus can be visibly seen. However, from the physiological point of view, the description will begin with the destruction of the corpus luteus and end with the destruction of the corpus luteus of the next cycle.

1. Follicular or Luteal Regression Phase (proestrus):

This 3-day period starts with the regression of the corpus luteus of the previous cycle and ends with the manifestation of the estrus. When the corpus luteus is destroyed, there is a fall in progesterone levels and, later on, a luteal tissue loss; in this process, the PGF2α of a uterine origin is the main luteolytic agent in domestic animals and most rodents.

As a result of the decline in progesterone levels, the negative feedback of this hormone at the hypothalamus level decreases as well and the pulsatile frequency of the gonadotrophic hormones (FSH and LH) starts to increase, stimulating the follicular growth with the development of a large follicle and the increase in estradiol levels.

When estrogens reach a certain level, the receptivity to the male becomes stimulated and the estrus cycle starts.

2. Periovulatory Phase (estrus and metaestrus)

This phase starts with the receptivity to the males (the cows allow both cows and bulls to mount them) and involves all changes allowing for the ovulation and the beginning of the corpus luteus formation.

During the estrus, lasting 18+/−6 h, the cow shows restlessness and anxiety, bellows frequently and loses appetite. In the case of dairy cows, milk production becomes affected. The cows show a vaginal mucus discharge, whose smell appeals and excites the bull (presence of pheromones), vulva edema and an increase of the myometrial tone of the uterus, easily detected by transrectal palpation.

During this phase, the high concentrations of estrogens reach the stimulation threshold of the hypothalamic cyclic center, stimulating the hypothalamic neurons to produce the GnRH peak and consequently, the LH peak. As regards the FSH, its secretion decreases as a result of the negative feedback of the estrogens and the inhibin, except for the moment when the LH preovulatory peak occurs where a FSH peak can appear. Later, 4 to 12 hours after the LH wave, basal concentration and the FSH pulse width increase, and this process is related to the first wave of follicular growth.

From 12 to 24 hours after estrus beginning, the cow's nervous system becomes refractory to estradiol and the psychic manifestations of the estrus come to halt.

The period immediately following the end of the estrus is called metaestrus (6 days). During this period, the ovulation of the cow occurs, unlike other species that ovulate during the estrus, giving rise to cell organization and the development of the corpus luteus. Ovulation occurs 28 to 32 hours after beginning of the estrus and is unleashed by the LH preovulatory peak. Ovulation is followed by a deep bleeding and the follicle is filled with blood and becomes a hemorrhagic body.

While the corpus luteus is formed (luteinization), a series of morphological and biochemical changes occur, allowing follicular cells to transform into luteal cells. These changes end on the seventh day with the formation of a functional corpus luteus.

3. Luteal Phase (diestrus):

This phase is characterized by the predominance of the corpus luteus. The maintenance of the corpus luteus as well as the progesterone synthesis are related to the progesterotrohic and luteotrophic LH hormone.

Other hormones taking part in the progesterone synthesis are FSH and PGI2. The FSH hormone would apparently join to receptors located in the corpus luteus and would cause an increase in progesterone secretion. As regards PGI2, in addition to stimulating luteal cells to produce progesterone, it may increase the blood flow at the ovarian level, having a positive effect on the synthesis and secretion of progesterone.

If the ovum IS not fertilized, the corpus luteus remains functional until Day 15–20, after which regression starts in order to prepare for a new estrus cycle.

FOLLICULAR DYNAMICS OF THE ORGANISMS

The growth and regression process of antral follicles leading to the development of a preovulatory follicle is known as follicular dynamics. There are between 1 and 4 follicular growth and development waves during the estrus cycle of the bovines and the preovulatory follicle derives from the last wave.

In order to describe the follicular dynamics of the bovines, it is necessary to define the concepts of recruitment, selection and dominance:

Recruitment: The process by which a cohort of follicles starts to mature in an environment with an adequate contribution of gonadotropins allowing for ovulation.

Selection: The process by which one of the follicles is selected, avoids the atresia and is likely to reach ovulation.

Dominance: The process by which the selected follicle dominates by exercising a inhibitory effect on the recruitment of a new cohort of follicles. This follicle becomes considerably bigger in size than the rest, is responsible for a higher estradiol secretion and acquires the capacity to continue developing in a hormonal environment that would be adverse for the rest of the follicles.

The cause of the regression of the dominant follicles of the first waves (1 out of 2 waves, and 2 out of 3 waves)

seems to be the presence of low-frequency LH pulses due to the high levels of progesterone, which would result in a reduced androgen synthesis and consequently a reduced estradiol synthesis, giving rise to the beginning of the follicular atresia.

RESUMPTION OF THE ACTIVITY AFTER CALVING

Follicular activity is normally absent in the first 10 days after calving, but starts to resume quickly after this period.

In well-fed dairy cows, the follicular wave activity is accompanied by follicular dominance. Therefore, it is common to find estrus onset and ovulation ten days after the calving. Beef cows follow a similar path. Resumption of the follicular waves has been observed ten days after calving. However, ovulation occurs later than in dairy cows (30.6 days in average).

In cows with an inadequate body condition and/or poorly fed, the follicular activity resumes also 10 days after calving in dairy cattle or about 30 days in beef cattle, but dominance can be absent for several weeks. In some primiparae, as many as 11 follicular waves were observed before a dominant follicle could finally ovulate.

PROGESTERONE ROLE IN THE ESTRUS CYCLE CONTROL

Exposure to high progesterone levels followed by its decline (progesterone priming) seems to be pre-requisites for a normal differentiation of granulosa cells, a normal expression of the estrus and the post-ovulatory development of the corpus luteus with a normal luteal phase. This mechanism involves the effect produced by an increase in LH pulse frequency on the production of follicular estrogens, the development of LH receptors and the luteinization. The presence of a progesterone exogenous source imitates the inhibiting action of this hormone's luteal levels on the LH pulsatile secretion, with the suppression of the dominant follicle growth and the resulting synchronic development of a new follicular development wave. The removal of this exogenous progesterone source allows for the increase in frequency and width of LH pulses and the growth of a dominant follicle, which will ovulate 48 to 72 hours later.

The use of intravaginal devices impregnated with progesterone is a common practice in animal production in order to synchronize the estrus in an organism, such as bovines (both dairy and beef), swine, equine and the like.

The use of a device results in a good synchrony of fertile estrus and becomes an essential tool for fixed-time artificial insemination patterns as well as for prefixed-time artificial insemination with a short period of estrus detection (36, 48 and 72 hours).

Artificial insemination costs, heavily influenced by the use of the products required for synchronization, have frequently restricted the application of this technology. Therefore, a significant effort was required to achieve an affordable cost level for the producers.

In this respect, the use of intravaginal devices, unlike other progestagens, offers the possibility of re-use and this results in a considerable cost reduction given the relative weight of progestagens on the remaining AI (Artificial Insemination) inputs.

For example, a profitable production of beef or milk often requires a maximum reproductive efficiency in today's competitive market.

The factors contributing to this profitability are said to be: early services, high pregnancy rates, low prenatal losses, short lactation periods, high conception rates after early weanings and low frequency of anestrus animals.

Only a planned reproductive management can ensure good results in the abovementioned parameters and this requires an estrus control and/or synchronization system that can additionally improve the reproductive rates mentioned above.

Nowadays, the technology required to plan and control the estrus is available and affordable to the producers, who can get good results without modifying their operation management practices.

Several methods were used to control reproductive cycles, including products that interrupt the cycle by suppressing the ovarian activity (progestagens), products causing the regression of the corpus luteus (prostaglandins) or agents inducing and synchronizing the follicular development and the ovulation (combination of estrogens, progestagens and prostaglandins, PMSG, HSG, GNRH, and the like).

The use of estrogens, progestagens and prostaglandins provides the veterinarian with the necessary tools for a pharmacologically rational management of the estrus cycle, resulting in benefits such as the possibility of inseminating the animals on a fixed-time basis without estrus detection, recovery of animals with abnormal or absent estrus cycles and improvement of the overall fertility of the herd.

Earlier devices used to synchronize the estrus in cattle are typically known as CIDR (control of internal drug releasing) and were developed in New Zealand by the Ruakura Agricultural Research Centre and the Agricultural Division of the Carter Holt Harvey Plastic Products Group Ltd. Included within this range of devices is also the French PRID, developed by CEVA SANTE ANIMALE.

These devices consist of a nylon or coiled metal core (devoted to provide some rigidity to the device) covered with a Dow Corning 595 silicone elastomer containing 1.9 g (10% p/p) of progesterone.

Two US patents of a prior art device and process are disclosed U.S. Pat. Nos. 6,423,039 and 6,663,608.

The polymer used to make the CIDR device is a silicone of the vinyl-siloxane type (VMQ), reticulated using platinum as catalyst.

The PRID is a silicone elastomer coil with 1.55 g of evenly-spread progesterone and a gelatin capsule with 10 mg of estradiol benzoate.

The abovementioned intravaginal devices have generally the following characteristics:

a) The prior art devices have a progesterone dose over 1.5 g, typically 2 g, which increases considerably the cost of the inducing device;

b) The inductors of the prior art devices can be reused but in order to ensure a progesterone level over 1 ng/ml in blood plasma during 7 days (minimum level required to block the endogenous gonadotropins and allow for the effective synchronization of the dynamics of the follicle and the ovulation), both in use and reuse, additional injections of progesterone must be applied; in the case of the inductor containing an estradiol benzoate capsule (10 mg), the treatment is longer and takes at least 12 days.

c) The progesterone release curve (measured in plasma) in the first use vs. the length of time of the treatment with the prior art devices is significantly different from the one obtained during the prior art devices reuse.

d) The prior art devices are difficult to apply.

Further, various CIDR's are manufactured from a liquid polymer that includes vinyl groups, since the polymer is reticulated with platinum. This type of curing, known as curing per addition, involves a first-order reaction occurring at a high speed and providing a high reticulation density. As a result of this curing process, the silicone rubber matrix obtained is highly rigid. Therefore, the progesterone released from the prior art devices is often characterized by a low spreading speed and this requires impregnation of the device with high doses of progesterone to achieve an acceptable drug release level.

Accordingly, it is an objective of the present invention is to provide an improved and new estrus-inducing devices and processes combining the following advantages and characteristics compared to prior art:

a) It is an object of various embodiments of the present invention, either alone or in combination with other objectives, to provide a device and/or process that utilizes a lower dose of progesterone than the prior art.

b) It is an object of various embodiments of the present invention, either alone or in combination with other objectives, to provide a device and process that allows progesterone absorption over 1 ng/ml in plasma during a 7-day treatment cycle both during repeated uses.

c) It is an object of various embodiments of the present invention, either alone or in combination with other objectives, to provide for a device and process whereby the progesterone release curves (measured as progesterone in plasma) versus the length of time of the 7-day treatment cycle are similar.

d) It is an object of various embodiments of the present invention, either alone or in combination with other objectives, to provide a device and process whereby an initial content of progesterone and a residual content of progesterone after use is comparable between repeated use(s) of the device.

e) It is an object of various embodiments of the present invention, either alone or in combination with other objectives, to provide a device and process whereby supplementation of the progesterone content with progesterone injections is not necessary through at least one repeated use, thereby resulting in less stress and in an equal shift in the follicular maturation wave as compared to organisms receiving a supplemental progesterone injection.

SUMMARY OF THE INVENTION

Embodiments of the present invention generally relate to intravaginal devices containing progesterone that can be used as an estrus inductor in an organism, such as bovine, swine, equine, and the like. Further, embodiments of the present invention generally relate to processes of manufacture and use of said devices. Embodiments of the new devices of the present invention generally include the following characteristics, either alone or in combination:

a) An intravaginal anchoring structure. In various embodiments the anchoring structure comprises a cruciform and/or elastically deformable body, optionally with blind tubular branches defining a continuous inner duct connected to the outside through transversally-placed holes located along said tubular structure.

b) A nylon insert on said inner duct. In various embodiments, whose cross section together with the cross section of the inner duct define a free space along its surface.

c) A chamber located in the inner part of said cruciform body and, in various embodiments, connected to the outside by means of a hole.

d) In various embodiments, the anchoring structure consists of a phenyl-vinyl-silicone matrix reticulated with peroxide and homogeneously impregnated with about 1 g natural progesterone.

e) In a most preferred embodiment, but not meant as a limitation, the physical dimensions of the anchoring structure, free from substantial impregnation with progesterone, are as follows:

| | |
|---|---|
| Volume: | 25 cm3 +/- 1.5 cm3 |
| External area: | 135 cm2 +/- 5% |
| Internal area: | 92 cm2 + - 5% |
| Total area: | 230 cm2 +/- 5% |

An embodiment of a device according to the present invention illustrates considerable differences as compared to prior art devices.

For example, a comparison of progesterone release curves with device insertion times illustrates that various prior art CIDR devices (with 1.9 g of progesterone) produce plasma progesterone concentrations that cannot be quantified until hours after the application of the device, in some cases, whereas embodiments of the present invention (with 1 g of progesterone) produce progesterone levels of 3 to 4 ng/ml in as little as 0.5 hours after device application, in most cases.

Various embodiments of a device of the present invention are made from a phenyl-vinyl-silicone reticulated with a peroxide curing technique. Various processes of these embodiments require only a second-order reaction, with slower curing times. Since the reaction speed is slower, the silicone reticulation level can be easily controlled, resulting in a mesh with enough flexibility and elasticity to facilitate progesterone spreading towards the surface of various embodiments of the present invention, while retaining adequate mechanical properties, such as rigidity.

As a result of improved flexibility and elasticity of peroxide-reticulated matrices, the progesterone spreading speed increases and allows for impregnation of the device with a smaller drug amount.

Another improvement found in various embodiments of the present invention is that the presence of holes connecting with the inner duct and the external surface allows progesterone to spread by following two alternative paths: (1) towards the external surface of the device; and, (2) towards the internal surface of the inner duct, from which the progesterone may spread along the inner duct towards communicating holes and through them to the outside or exterior of the device whereas the prior art CIDR devices only allow progesterone to spread towards the external surface.

A further improvement of various embodiments of the present invention is that at least one branch or at least one portion is larger than the respective portion or branch. By respective portion and/or branch is meant the branch and/or portion that extends from the intersection of the middle portion and the respective branch and/or portion. Such an arrangement allows a better anchor in the vaginal duct and/or more security in terms of any possible displacement of the device towards the outside during use/application. This improved rigidity in the side branches of the longitudinal shaft is accompanied by a higher flexibility in the opposing side branches. Further, the particular rigidity and flexibility of the present invention can be regulated through modification of the nylon core and/or curing processes.

Other embodiments of the present invention may also include at least one chamber inside or within the exterior of the device that is connected to the outside by means of a hole and/or passage which may be optionally sealable. A chamber of such embodiments may be utilized to contain supplementary additives to be used with the device, such as hormones, drugs, antiseptics, lubricants, and the like.

Further included within the scope of the present invention are processes related to estrus synchronization and processes for manufacture of various embodiments of the present invention.

DETAILED DESCRIPTION OF THE INVENTION

Figure 1:
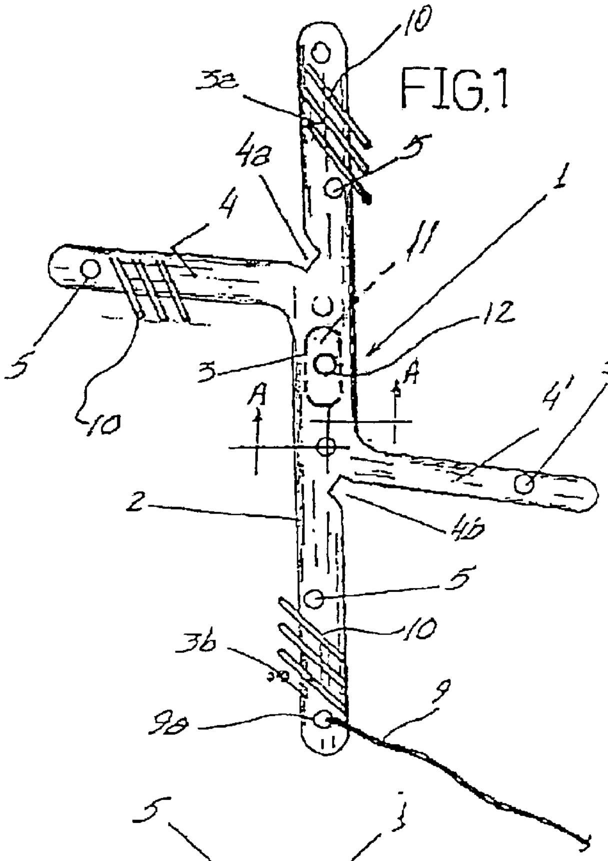
FIG. 1 illustrates a top view of an embodiment of the intravaginal device that is the object of the present invention.
Figure 3:
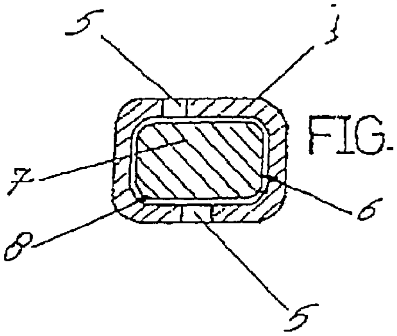
FIG. 3 shows a cross-section view through line A—A of FIG. 1
Figure 2:
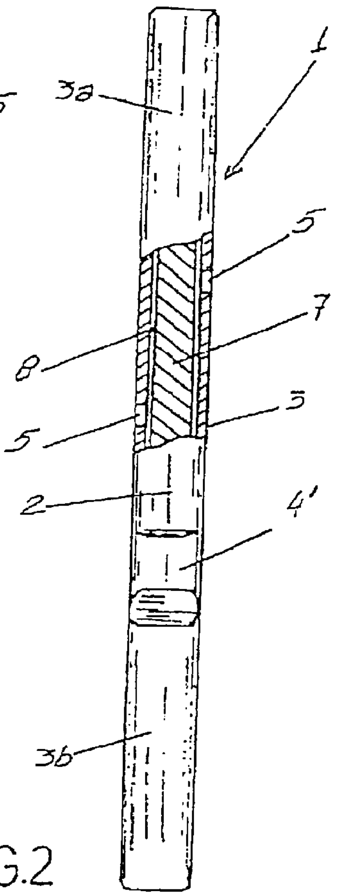
FIG. 2 illustrates a partially cut longitudinal front view of the device of FIG. 1.

According to the illustration included in the drawings, specially with reference to FIG. 1, embodiments of a device of the present invention include an irregular and hollow cruciform piece (1), which can be made of vulcanized silicone, delimited by a longitudinal branch (2) consisting of a middle portion (3) that extends up and down in opposing portions, such as opposite, (3*a*) and (3*b*) mismatched between themselves according to a longitudinal shaft and extending themselves from the middle section (3) and from the intersection areas with said opposing portions (3*a*) and (3*b*). In various embodiments, branches (4) and (4') extend from about the intersection of middle portion (3) and the first opposing portion (3*a*) and/or the second opposing portion (3*b*). Branches (4) and (4') generally extend from middle portion (3) at an angle from about 0 degrees to about 180 degrees from respective intersection. In various embodiments, branches (4) and (4') are provided with transversal cuts (4*a*) and (4*b*) about the intersection of the respective portions and branches.

However portions (3*a*) and (3*b*) may oppose one another at any angle desired. Generally, all that is required is that portions (3*a*) and (3*b*) extend away from a middle portion (3). In certain embodiments, middle portion (3) will be the intersection of portions (3*a*) and (3*b*).

Likewise, branches (4) and (4') may extend at any angle away from middle portion (3). As well, in various embodiments, branches (4) and (4') extend away from one another in other than a parallel orientation. In certain embodiments, middle portion (3) is the intersection of branches (4) and (4').

In other embodiments, the size of branches (4) and (4') and/or portions (3*a*) and (3*b*) may be varied. For example, in various embodiments, branch (4) has a larger section than branch (4'), often resulting in a lower flexibility. Likewise, portions (3*a*) and (3*b*) may be of different sizes, resulting in or not resulting in varying flexibility.

In an embodiment, the free extremes or ends of portions (3*a*) and/or (3*b*); and/or, of branches (4) and/or (4') of the piece (1) are substantially sealed with the upper and lower faces of the piece (1) containing or having a series of holes (5) extending from about inner duct (6) of the piece (1) and communicating with the exterior of the device.

In various embodiments, piece (1) has a nylon core (7) extending longitudinally and defining together with the inner annular surface of duct (6) a free space (8) with a circular crown shape. However, other suitable materials will be readily apparent to those of ordinary skill in the art, such as other thermoplastics and the like. Moreover, the special arrangement of free space (8) may be varied.

In various embodiments, a passing hole (9*a*) is located on a portion or branch of the device. In a preferred embodiment, an end of portion (3*b*) and/or (3*a*) has a passing connection (9*a*), such as a hole and the like, to secure a thread (9) to remove the intravaginal device from the organism after insertion. In various embodiments, thread (9) is nylon. However, other suitable materials will be readily apparent to those of ordinary skill in the art.

In various embodiments, device (1) has strips (10) along portions (3*a*) and/or (3*b*); and, (4) and/or (4') designed to guide and anatomically attach the device to the vaginal duct. In a preferred embodiment, at least one branch and/or portion has no strips (10). Strips (10) may generally be any surface to increase a coefficient of friction between device (1) and a vaginal duct upon insertion, such as narrow elongated additions, roughened surfaces, exterior elements, separate elements, and/or the like.

In various preferred embodiments, device (1) has a longitudinal branch (3) with a chamber (11) inside, connected to the outside by means of a hole (12) for receiving additional injections of medicaments, such as aforementioned, later mentioned, and the like.

The present invention also contemplates processes for synchronizing estrus and processes for utilizing a device of the present invention to synchronize estrus. Generally a process to utilize embodiments of the present invention is as follows:

A process for the use of an intravaginal device for estrus synchronization comprising the steps of:

inserting a device into a vagina of an organism comprising an intravaginal anchoring system comprising a middle portion, a first opposing portion, a second opposing portion, a first branch and a second branch wherein the first and second opposing portions extend from the middle portion and the first branch extending from the middle portion at about an intersection of the first opposing portion and the middle portion and the second branch extending from the middle portion at about an intersection of the second opposing portion and the middle portion; a chamber located about the middle portion; at least one hole in at least one of the first opposing portion, the second opposing portion, the first branch and/or the second branch; and, a free space located within the anchoring system and connected to the chamber and the at least one hole;

leaving the device in the organism for between 3 and 7 days; and, removing the device. Further embodiments may further comprise attempting to artificially inseminate the organism after removing the device. Further embodiments may further comprise the step of reusing the device if the organism was not inseminated. Further embodiments may further comprise reusing the device further comprises sliding a sheath on the device. Further embodiments may further comprise injecting a medicament in the device. Further embodiments may further comprise progesterone. As well, the time may be as large as 100 days that the device is left inserted.

Other embodiments of the present invention may be described by:

An intravaginal device comprising:

an intravaginal anchoring system comprising a middle portion, a first opposing portion, a second opposing portion, a first branch and a second branch wherein the first and second opposing portions extend from the middle portion and the first branch extending from the first opposing portion and the second branch extending from the second opposing portion;

a chamber located within the middle portion;

at least one hole in at least one of the first opposing portion, the second opposing portion, the first branch and/or the second branch; and, a free space located within the anchoring system and connected to the chamber and the at least one hole.

And further including processes for using the same.

Further embodiments of the present invention incorporate a hollow tube (Not shown) for inserting the device in the vagina of an organism. The inside diameter of the tube is generally large enough to encompass embodiments of the device when folded. Embodiments of the device are folded when the first branch and the first portion are generally aligned. Such folding may occur by malformation by an operator, prepackaging, and the like. Generally, the device is malformed to allow insertion into the hollow tube for insertion into the organism. In various embodiments, a rod may be used to aid in pushing the device into the hollow tube.

For inserting the device into an organism, an operator may take insert an end of the hollow tube into the vagina of an organism. The rod may then be used to push the device from the hollow tube into the vagina of the organism. Upon exiting the hollow tube, the first branch and the second branch will revert from the malformed state. The spatial arrangement of the first and second branches and the first and second portions will act to create friction between the ducts of the vagina and the device, thereby resisting removal. Further resistance, or an increase in the coefficient of friction between the ducts of the vagina and the device may be achieved by adding strips to the branches and/or portions.

In various embodiments, a thread extends out of the vagina and may be grabbed by an operator for removal of the device.

In various embodiments, a device of the present invention is specifically designed for a use and a reuse without medicament supplementation, such as progesterone. Further embodiments may accept a sheath for further reuse.

Figure 4:
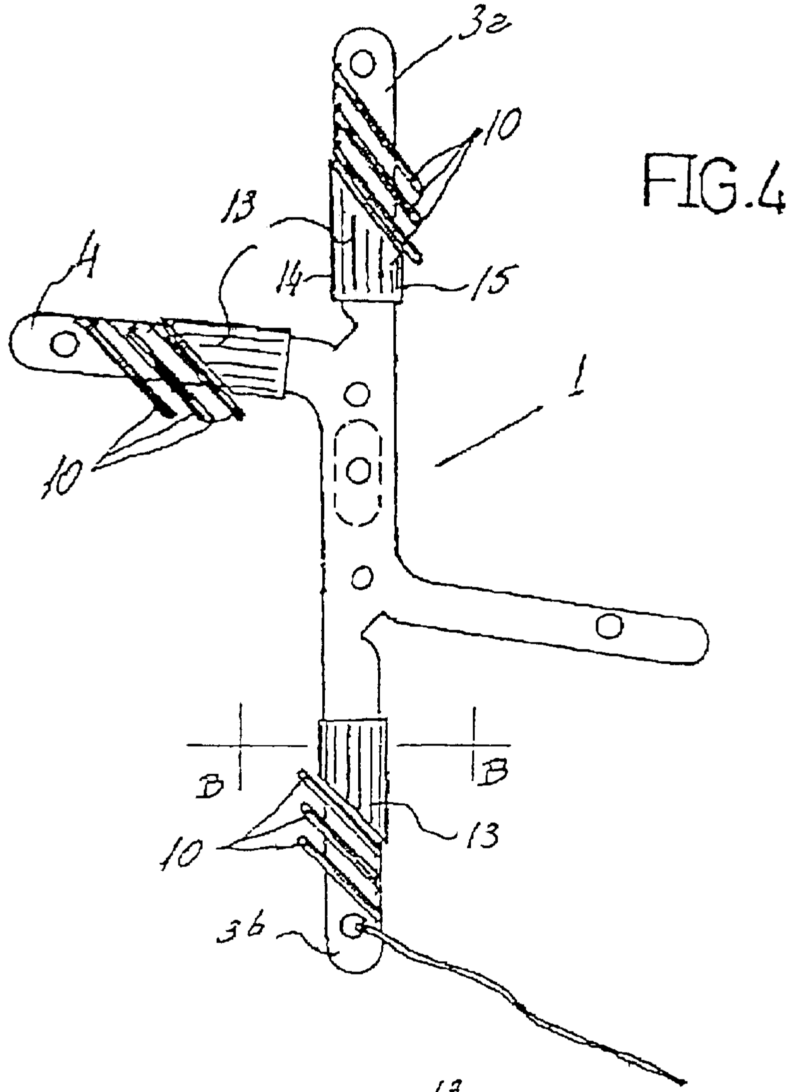
FIG. 4 shows a top view of the device included in FIG. 1 with embodiments of accessories for multiple repeated uses.

FIG. 4 illustrates sheaths (13) that may be used in various devices upon reuse. In a preferred embodiment, sheaths (13) are slid over ends of any of the branches and/or portions, past strips (10).

Figure 5:
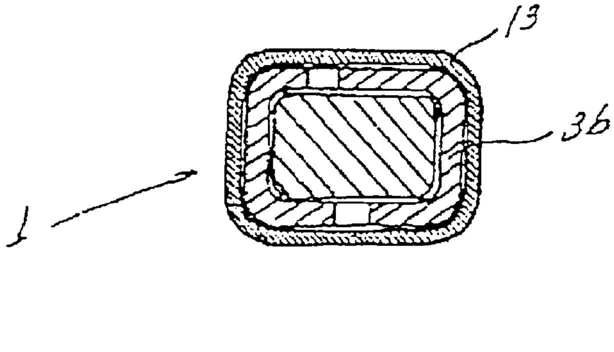
FIG. 5 shows a cross-section view through line B—B of FIG. 4.

In various embodiments, sheaths (13) have a rectangular trapezoidal longitudinal section with a large edge (4) and a small edge (15), as illustrated in FIG. 4, and a transversal section crossed by line B—B in FIG. 4, where sheath (13) is represented as applied on branch **(3*b*) of the device 1, as illustrated in FIG. 5. However, sheath(s) (13)** may be of any size and/or shape.

In various embodiments, sheaths (13) may be tightly applied about branches (**3*a* and/or 3*b*; and/or, 4 and/or 4') and resist removal from device (1). In other embodiments, sheath (13) may be at least partially loose about the portions and/or branches whereby sheath (13) may slide about the portions and/or branches. In preferred embodiments, sheath(s) (13)** are slid onto a branch and/or a portion. However, other methods of application may be utilized.

EXAMPLES

The following examples are meant as illustrative and not as a limitation on the scope of the claims. For an understanding of the scope of the invention, reference should be had to the appended claims.

Mechanism of Action of the Device That is the Purpose of the Present Invention

The progesterone released by the device that is the object of the present invention is structurally identical to the endogenous progesterone and plays an important role in the ovarian follicular dynamics. The supraluteal levels (>1 ng/ml) obtained a few minutes after the insertion of the device cause the regression of the dominant follicle and speed up the replacement of the follicular waves. This ceasing of the secretion of the follicular products (estrogen and inhibin) results in an increase in the FSH hormone responsible for the occurrence of the next follicular wave. On the other hand, the removal of the device results in a progesterone decline to subluteal levels (<1 ng/ml) inducing the LH pulse frequency increase and the growth and persistence of the dominant follicle with very high estradiol concentrations leading, on the one hand, to the estrus and, on the other, and at an endocrine level, to the LH peak followed by ovulation.

Reuse: Based on the results obtained in reuse tests carried out in ovariectomized animals, both in plasma and in the residual progesterone analyses of various devices of the present invention, devices of the present invention may be reused without endangering the efficacy of the treatment. Such reuse encompasses the reuse of the devices in the resynchronization of already synchronized animals that have not become pregnant and the like. Inseminations resulting from the practice of processes and with devices of the present invention may be expected to be at or about 3 to 4 days.

Estradiol Role in the Estrus Cycle Control

Estrogens are steroid hormones produced by the ovarian follicle and their synthesis can be explained as follows: The hypophysial Luteinizing Hormone (LH) interacts with its receptor placed in the cells of the inner theca and produces androgens. The latter pass through the basal membrane and enter the granulosa cells. Inside these cells, the hypophysial Follicle Stimulant Hormone (FSH) acts by stimulating an aromatase enzyme that transforms the androgens in estrogens, which pass on to the follicular fluid and to circulation in general. Later on, they get their target and act by means of the mobile receptor or intracellular model. The estrogens act on different target organs, such as the Fallopian Tubes, the uterus, the vagina, the vulva and the central nervous system. At the level of the uterus, they act as trophic hormones causing the proliferation of endometrial cells and glands, which increase their secretion.

In the myometrium, they produce a hypertrophy of the circular and longitudinal muscular layer and sensitize their cells to the action of the oxytocin, favoring their contractibility and carrying capacity. They also produce congestion of the blood vessels with stroma edema. In the cervix, they produce relaxation, increase its diameter, and result in the appearance of an abundant and transparent mucus secretion. In the vagina and the vulva, blood vessels become congested and the edema appears. In the vagina, the epithelium growth is stimulated up to the cornification. In the Fallopian Tubes, growth and hypermotility are stimulated. In the central nervous system, estrus behavior is stimulated and in the hypothalamus, they produce a negative feedback on the tonic center and a positive feedback on the cyclic center.

The use of exogenous estradiol for estrus cycle control is designed to trigger the luteolysis when applied in the middle of the cycle or to prevent the growth of a new corpus luteus when applied after the ovulation. Likewise, when applied at the time of progestagen application, it suppresses the present follicular wave and induces the development of a new follicular wave in 3 or 4 days on average.

Mechanism of Action of Estradiol Benzoate

The Estradiol Benzoate is a synthetic derivative of 17β Estradiol, an steroid hormone synthesized by the ovarian follicle and developed to optimize reproductive results in treatments with progestagens in bovines.

The use of 2 mg Estradiol Benzoate at the time of application of the intravaginal device (considered as Day 0) causes the beginning of a new follicular wave. The application of 1 mg Estradiol Benzoate 24 hours after removal of the device leads to the luteolysis and induces a preovulatory LH peak through the positive feedback on the GnRH and the LH, leading to ovulation 70 hours after removal of the device. For this reason, it is an ideal tool for ovulation synchronization in fixed-time artificial insemination processes.

Prostaglandin Role in the Estrus Cycle Control

Prostaglandins are 20-carbon unsaturated fatty acids consisting in a pentane cycle with two aliphatic side chains. They are synthesized as from the free arachidonic acid present in most tissues of the body and serve as local hormones, acting on the tissues near the place of their synthesis. Prostaglandins are structurally classified in nine large groups, A to I, each one containing subgroups named with the subscripts 1, 2 and 3. In domestic animals, PGF2α seems to be the most important prostaglandin.

In the reproductive system, prostaglandins play a significant role in the ovulation and luteolysis processes, in the transportation of gametes, in the uterine motility, in the expulsion of fetal membranes and in the transportation of sperm. PGF2α causes a quick regression of the functional corpus luteus with a quick decline in progesterone production. Luteolysis is normally followed by the development of ovarian follicles and estrus with normal ovulation. In bovines, the estrus occurs 2–4 days after luteolysis and in mares, 2–5 days. The immature corpus luteus is insensitive to the effects of PGF2α and in bovines and equines this refractory period lasts the first 4–5 days after ovulation.

The precise mechanism of the luteolysis as induced by PGF2α is still uncertain but could be related to changes in the blood flow of uterus-ovarian veins, inhibition of the normal ovarian response to gonadotropins or stimulation of catalytic enzymes. Besides, PGF2α has a direct stimulating effect on the uterus smooth muscle, causing contraction and a relaxing effect on the cervix.

Mechanism of Action of Cloprostenol

Cloprostenol is a synthetic functional analog of prostaglandin PGF2α causing the quick regression of the corpus luteus with a quick decline in progesterone production. Luteolysis is normally followed by the development of ovarian follicles and return to estrus with normal ovulation. Estrus occurs 2 to 4 and 2 to 5 days after application in cows and mares respectively. The early corpus luteus is insensitive to PGs effects; this refractory period extends until 4 to 5 days after ovulation.

One or two doses of cloprostenol applied between 12 and 40 days after calving cause a better uterine involution and luteolysis, thus preventing silent estrus caused by a persistent corpus luteus and accelerating the return to normal cycles.

Rationale for the Use of eCG (PMSG) in Reproductive Therapies

The Equine Chorionic Gonadotropin (eCG, PMSG) is a glycoprotein hormone secreted in the endometrial cups of gestating mares approximately between Days 40 and 120 of pregnancy. From the endocrinological point of view, it is important to underline two valuable characteristics of the eCG that differentiate this hormone from other glycoprotein hormones: the first one is that it has FSH (follicle stimulating) and LH (luteinizing) activity when administered in species other than equines, where it only has LH activity; the second one is its high content of carbohydrates, a fact that provides this hormone with unique characteristics from the pharmacological point of view, such as a long half-life. This feature favors its use in a single dose unlike the FSH whose half-life is extremely short and requires several applications.

The use of eCG for veterinary purposes is therefore widely grounded from the endocrinological point of view and justified in situations requiring a therapy with exogenous gonadotropins, specially when a FSH effect is sought for, that is to say an stimulation of the follicle genesis in ovaries with reduced or absent activity.

Mechanism of Action of the Equine Chorionic Gonadotropin

Given its dual action (FSH/LH), the equine chorionic gonadotropin stimulates directly the follicular development and ovulation in most domestic species.

Progestagens, used in many species on a preliminary basis, inhibit the release of the luteinizing (LH) and follicle stimulating (FSH) hormones of the hypophysis, curbing the follicular development and the ovulation until the desired time. When progestagens are removed, blood progesterone concentration falls quickly, after which the animal can fall in heat. The administration of the equine chorionic gonadotropin at that moment leverages the endogenous gonadotropins stimulation of the follicular development and ovulation. Therefore, it becomes an excellent tool to be used specially in those cases in which these functions can be endangered (post-calving or nutritional anestrus).

Results Obtained in Field Tests

| Category | Treatment Animal # | Day 0 | Day 7 | Day 8 | Day 9 | Day 10 | Pregnancy % |
|---|---|---|---|---|---|---|---|
| Bradford Heifer | 40 | ID + BE2 | | RD + PG | BE1 | IAS | 52.5 |
| Dry cow | 48 | ID + BE2 | | RD + PG | BE1 | IAS | 62.5 |
| Aberdeen Angus Heifer | 50 | ID + BE3 | RD + PG | BE1.5 | IAS | | 88.5 |
| Dry cow | 39 | ID + BE2 | eCG250 UI + PG | RD + PG | BE1 | IAS | 61.0 |
| VTP Hereford | 206 | ID + BE2 | | RD + BE1 | | IAS | 66.5 |

-continued

| Category | Treatment Animal # | Day 0 | Day 7 | Day 8 | Day 9 | Day 10 | Pregnancy % |
|---|---|---|---|---|---|---|---|
| VTP Brangus | 40 | ID + BE2 | | RD + PG + DT | BE1 | IAS | 47.5 |
| Heifer | 25 | ID + BE2 RD + PG | | BE1 | IAS | | 52.4 |
| | | | | | | | 61.5% |

References:
ID = Device Insertion
BE1 = Estradiol Benzoate 1 mg
BE2 = Estradiol Benzoate 2 mg
BE3 = Estradiol Benzoate 3 mg
RD = Device Removal
PG = Prostaglandin application
eG250 = Application of 250 IU Equine Chorionic Gonadotropin
IAS = Systematic Artificial Insemination
VTP = Cow with calf at the foot
DT = Temporary Weaning Curve of plasma progesterone release with new and used devices. Study of residual progesterone in new and used devices.

The purpose of this study was to compare plasma progesterone profiles in bovines treated with new and used devices and to determine the residual progesterone content in used and reused devices. The study included ovariectomized animals, that is to say animals deprived of their natural progesterone source. Likewise, samples were taken of new and used devices to evaluate the progesterone content before and after use and repeated use(s).

Materials and Methods

Animals: The study included Aberdeen Angus cows, 3–4 years old, with a 3 body condition (scale 1–5). These animals were ovariectomized 30 days before the trial. The animals were randomly divided in two groups, one receiving new devices and the other one, used devices.

Treatment: The devices were inserted in the vagina of the animals (Time 0) and removed on Day 7 after insertion.

Sampling: The animals were sampled at Time 0 (before insertion) and at 0.5 h, 2 h, Day 1, Day 2 and Day 7+12 hours after removal of the device. Heparinized blood samples were centrifuged and the plasma obtained was stored at −20° C. until the analysis.

Analyses: Analyses were carried out on the devices and the plasma samples. In the case of the devices, we evaluated the progesterone content before and after insertion in the vagina, both for new and used devices. This analysis was carried out after extraction with organic solvent in Soxhlet equipment by means of a chromatographic method (HPLC). The quantification of progesterone in plasma samples was done by means of a specific ELISA test.

Results:

Table I illustrates the results obtained in plasma samples, expressed in ng/ml of progesterone:

TABLE I

| | Time | | | | | | |
|---|---|---|---|---|---|---|---|
| | 0 h | 0.5 h | 2 h | 1 day | 2 days | 7 days | +12 h |
| New | 0.29 | 3.63 | 4.67 | 5.53 | 6.80 | 2.45 | 0.25 |
| Used | 0.20 | 3.00 | 3.50 | 4.00 | 4.80 | 1.78 | 0.20 |

Table II illustrates the results obtained in the evaluation of progesterone content in a device sample before and after use and reuse, expressed in mg of progesterone per device. (Averages of all devices used are included).

TABLE II

| Initial progesterone 1st use (mg) (1) | Residual progesterone 1st use (mg) (2) | Differences (mg) 1 − 2 |
|---|---|---|
| 1080 | 641.5 | 438.5 |
| Initial progesterone 2nd use (mg) (3) | Residual progesterone 2nd use (mg) (4) | Differences 3 − 4 |
| 641.5 | 198.5 | 443 |

No significant differences are observed in plasma progesterone levels between animals treated with either new or used devices. Plasma progesterone levels in both groups of animals remained, during the 7-day period of the trial, over 1 ng/ml, minimum level required to block the endogenous gonadotropins and allow for an effective synchronization of the follicular dynamics and ovulation.

The content difference between initial and residual progesterone is similar in both devices (new and used) (438.5 mg and 443 mg). This shows that the device of the present invention effectively absorbed hormone through the vaginal mucosa was similar in both cases, and this is compatible with the similarity found in the plasma release curves observed.

Based on the results obtained in use and reuse tests in ovariectomized animals, both in the plasma progesterone analysis and in the study of residual progesterone found in the devices, we can conclude that the devices can be reused without endangering the effectiveness of the treatment. This includes the reuse of the devices both in the synchronization and the resynchronization of already synchronized animals that have not become pregnant.

As indicated above, the results of plasma progesterone release curves illustrated in Table I show that the device can be reused, that is to say applied for a second consecutive time without the need of any modification or additional substitution.

After the second use, as shown in Table II, the device removed from the animal still maintains a progesterone content of around 200 mg.

In various embodiments, a device can only be reused once because the progesterone level is not high enough for another reuse. Other embodiments start with a higher initial concentration of progesterone and can be reused multiple times.

For example, in an embodiment, Applicants have found a way to use the device after reuse for a third consecutive time.

The method consists in supplying the exhausted device after the second use with at least one, preferably a least three sheaths made of the same material as the device, and impregnating each with about 100 mg of progesterone.

In an embodiment, each of these sheaths weighs approximately 2.9 g, its wall thickness is 1.5 mm and includes a rectangular trapezoidal longitudinal section with a 3 cm large base and a 1.5 cm small base. However, varying other sheaths may be used.

Besides, these sheaths have a cross-section that adapts to the cross-section of the three branches of the cruciform device fitted with guiding strips.

After the second use (reuse) of the device, these sheaths or sleeves are inserted fully into the three branches of the device having strips, in such a way that they remained secure by pressure and cannot be accidentally removed because of the presence of the guiding strips.

Each sheath has 100 mg of progesterone and that the device after reuse has around 200 mg, therefore a device upon reuse with sheets has about 500 mg of progesterone.

It has been illustrated that the modified device can be used for a third consecutive time with similar performance to that obtained during the first and second use of the device.

Field Tests with Reused Devices in Estrus Synchronization in Bovines

1. Experiment with Heifers:

Animals used: 98 Hereford heifers, 15 month old, with a body condition ranked as 3 (in a 1–5 scale) with cycles determined by palpation and 12 days later by ultrasonography.

Work Protocol: On Day 0, the device was inserted +2 mg Estradiol Benzoate. Half of the animals (at random) received used devices. On Day 7, the devices were removed and the animals received an injection with 1 ml prostaglandin. On Day 8, 1 mg Estradiol Benzoate was applied and 24 hours later (54 hours after removal of the device), the fixed-time artificial insemination was performed. Thirteen (13) days after the AI, the devices were reinserted and then removed on Day 20. On Day 21, 0.5 mg Estradiol Benzoate was applied and the estrus was detected up to Day 25.

Results Obtained:

| Treatment | Amount of Animals | Return to estrus | % Non-return |
|---|---|---|---|
| New devices | 49 | 14 | 71.4 |
| Used devices | 49 | 12 | 75.5 |

2. Experiment with Cows

Animals used: 10 dry cows, body condition 3 to 3.5

Work protocols: On Day 0, the device was inserted +2 mg Estradiol Benzoate. On Day 7, the devices were removed and 1 ml prostaglandin was injected. On Day 8, 1 mg Estradiol Benzoate was applied and 24 hours later the fixed-time artificial insemination was performed. All the animals received used devices.

Results Obtained:

| Bull | Amount of Animals | Pregnant | Empty | % Pregnant |
|---|---|---|---|---|
| Bull A | 25 | 12 | 13 | 48 |
| Bull B | 18 | 8 | 10 | 44.4 |
| Bull C | 43 | 14 | 29 | 32.5 |
| Bull D | 15 | 9 | 6 | 60 |
| Total | 101 | 43 | 58 | 42.5 |

Remarks: We observed a significant difference in the pregnancy percentage of animals inseminated by Bull C as compared to the rest, which could be attributed to a low fertility rate in the semen.

General Conclusions

It was illustrated that the progesterone levels of the devices of the present invention after one use are enough to generate a similar plasma release curve as compared to previously unused devices. This observation was confirmed by the evaluation of progesterone residual levels found in the devices after one or two uses, evidencing, in an embodiment, that approximately 400 mg progesterone is the amount effectively absorbed in both uses and that it is sufficient to keep levels over 1 ng/ml during the 7-day work protocol.

Field experiments on the estrus synchronization carried out with used devices and following conventional protocols have generated similar results to those obtained with new devices. This observation is consistent with the information included in the previous paragraph in the sense that the performance and the effectiveness of new and used devices are similar.

The device can be reused in estrus synchronization as well as in the resynchronization of already synchronized animals without affecting reproductive rates but reducing significantly Artificial Insemination costs.

Estrus synchronization systems consisting of intravaginal devices impregnated with progesterone and combined with estrogens (estradiol benzoate), prostaglandins and eCG and processes according to the present invention are the most efficient tools to implement a planned reproductive system. Such system may be used by, but not by way of exclusion, producers and veterinarians. Embodiments of the present invention optimize quickly the reproductive efficiency of the estrus through an improvement of the estrus detection tasks, therefore resulting in an increase in pregnancy rates per service, a significant reduction in open cow days and the possibility of achieving a 12.5-month interval between calvings. As well, these systems give the vet the therapeutic tools required to treat pathologies such as silent estrus, cystic ovaries or anestrus, which could endanger the fulfillment of the abovementioned objectives. Various embodiments of the present invention also encompass a procedure to manufacture the device characterized by:

a) in a mixing roll mill, where rolls turn in opposite directions and at different speeds, the following components must be added at a temperature between 50 and 90° C.:

100 parts by weight of phenyl-vinyl-silicone rubber without reticulation, with a hardness of 50° Shore;

1 to 2 parts by weight of powder dicumyl peroxide 1 part by weight of powder progesterone, and optionally, up to 0.05 parts by weight of a coloring, inorganic and inert pigment.

b) The mixture must then be subject to shearing to get its complete plastification and homogenization.

c) The sheets of the homogenous material formed must be recovered and stored.

d) A specific amount of the material obtained in c) must then be molded by injection-transfer. The composition of the material includes the amounts of silicone and progesterone corresponding to the final device, where the mould contains housings that ensure the centeredness of the plastic nylon insert.

e) The mould must then be kept at a temperature between 150 and 190° C. up to the end of the curing process.

f) The device must be removed from the mould and post-cured in a furnace at 150-190° C. during 4–8 hours.

g) The device must be recovered and packed in an inviolable packaging protected against UV.

However, the exact amounts of material, temperatures, and proceses may vary.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims. Further, all patents mentioned herein are herby incorporated by reference.

We claim:

1. An intravaginal device comprising:

an intravaginal anchoring system comprising a middle portion, a first opposing portion, a second opposing portion, a first branch and a second branch wherein the first and second opposing portions extend from the middle portion and the first branch extending from the first opposing portion and the second branch extending from the second opposing portion;

a chamber located within the middle portion;

at least one hole in at least one of the first opposing portion, the second opposing portion, the first branch and/or the second branch; and, a free space located within the anchoring system and connected to the chamber and the at least one hole.

2. The device of claim 1 further comprising progesterone.

3. The device of claim 1 further comprising at least one strip on at least one of the first and second opposing portions and/or the first and/or second branch.

4. The device of claim 1 further comprising a thread attached about an end of the second portion.

5. The device of claim 1 wherein the middle portion is an elongated tubular member.

6. The device of claim 5 wherein the first and second opposing extend opposite from the ends of the middle portion.

7. The device of claim 5 wherein an angle at the intersection of the first opposing portion and the first branch is about 90 degrees.

8. The device of claim 1 further comprising a sheath.

9. The device of claim 1 further comprising a hollow tube for loading the device into the vagina of an organism.

10. The device of claim 1 further comprising a thread.

11. The device of claim 1 wherein at least one branch or at least one portion is larger than the respective portion or branch.

12. A process for the synchronization of an organisms estrus cycle comprising the steps of:

inserting a device into a vaginal duct of an organism comprising the device of claim 1;

leaving the device in the organism for between 1 and 100 days; and, removing the device.

13. The process of claim 12 further comprising attempting to artificially inseminate the organism after removing the device.

14. The process of claim 13 further comprising the step of reusing the device if the organism was not inseminated.

15. The process of claim 14 wherein the step of reusing the device further comprises sliding a sheath on the device.

16. The process of claim 14 wherein the step of reusing the device further comprises the injecting a medicament in the device.

17. The process of claim 12 wherein the device has a medicament.

18. The process of claim 17 wherein the medicament is progesterone.

19. The process of claim 12 wherein the device is left in the organism between 3 and 7 days.

20. A process for the synchronization of an organisms estrus cycle comprising the steps of:

inserting a medicament containing device, comprising an inner duct, an external surface, at least one hole, and at least one communicating hole, wherein the at least one hole connects the inner duct to the external surface, the inner duct extending to the at least one communicating hole, within the vaginal duct of an organism, whereby the device allows progesterone to flow along two alternate paths, from the inner duct to the exterior surface of the device and towards the internal surface of the inner duct, from which the medicament is able to flow through the communicating holes to the vaginal duct.

21. The process of claim 20 wherein the medicament is progesterone.

22. The process of claim 20 wherein the medicament is contained within the device of claim 1.

* * * * *